(12) United States Patent
Bunin et al.

(10) Patent No.: US 8,006,321 B2
(45) Date of Patent: Aug. 30, 2011

(54) DISPOSABLE WOMEN'S PANTY

(76) Inventors: Simona Bunin, Parkland, FL (US); Sherene Costanzo, Parkland, FL (US)

( * ) Notice: Subject to any disclaimer, the term of this patent is extended or adjusted under 35 U.S.C. 154(b) by 48 days.

(21) Appl. No.: 12/006,471

(22) Filed: Jan. 4, 2008

(65) Prior Publication Data
US 2009/0172868 A1  Jul. 9, 2009

(51) Int. Cl.
*A41B 9/04* (2006.01)
(52) U.S. Cl. ... 2/406; 604/393; 604/385.03; 604/385.28
(58) Field of Classification Search .............. 2/400–408; 604/322, 329, 331, 346–348, 351, 385.19, 604/385.101, 940, 355, 339, 385.03–385.28, 604/387, 393
See application file for complete search history.

(56) References Cited

U.S. PATENT DOCUMENTS

| 4,205,679 | A | * | 6/1980 | Repke et al. | 604/366 |
| 5,613,964 | A | * | 3/1997 | Grenier | 604/385.01 |
| 5,810,800 | A | * | 9/1998 | Hunter et al. | 604/385.23 |
| 6,375,643 | B1 | * | 4/2002 | Moorhead et al. | 604/322 |
| 6,540,730 | B1 | * | 4/2003 | Niedermeyer | 604/385.27 |
| 6,936,038 | B2 | * | 8/2005 | Tears et al. | 604/385.04 |

* cited by examiner

*Primary Examiner* — Gloria Hale

(57) ABSTRACT

A disposable, substantially non-absorbent undergarment has a crotch region in combination with, and onto which a sanitary napkin or panty liner member is attached. Upraised side ridges bounding the crotch region of the panty both eliminate leakage, without adding to bulk of the undergarment, and present a defined area where at least one panty liner unit of the panty liner member is attached.

10 Claims, 3 Drawing Sheets

DISPOSABLE WOMEN'S PANTY

FIELD OF THE INVENTION

The present invention is a disposable panty undergarment for women. More particularly, the disposable panty is to be used during the menses period, is substantially non-absorbent, and is to be used in combination with at least one disposable sanitary napkin, or panty liner.

BACKGROUND OF THE INVENTION

A number of articles have been created and developed for absorbing and/or containing bodily fluids. For those articles that are addressed to the issue of bodily fluids produced during menstruation, a commonly used sanitary napkin is placed onto the interior of a woman's undergarment to protect that undergarment and adjacent garment(s) that the woman wears. This type of ordinary napkin, or panty liner, comprises an inner layer of absorbent material which is worn next to the body, and further comprises a substantially fluid impervious outer layer that is between the absorbent material and the undergarment. The outer layer is constructed to prevent leakage of the menses from the absorbent material to the undergarment and adjacent garments.

A number of articles directed to this field of invention, while addressing the particular needs stated therein, have a variety of problems associated therewith. One significant problem is despite the attempts of others to provide a liner that absorbs without leakage, leakage still occurs. For example, the devices disclosed in the patents to Poulsen, U.S. Pat. No. 2,929,379; to Testa, U.S. Pat. No. 3,367,334; and to Grenier, U.S. Pat. Nos. 5,429,631 and 5,613,964. Generally, these prior art devices teach the use of a plurality of stacked sanitary napkins such that when the uppermost napkin is soiled, it is removed to expose the next fresh unit for use. The problem with these types of devices is age-old as leakage still occurs. Additionally, the bulkiness of the respective devices causes unwanted bulging of the wearer's adjacent garments so as to appear unsightly and uncomfortable.

In an attempt to resolve the problem of leakage, still others have devised absorbent articles used in conjunction with secondary absorbent articles. Some examples of these devices can be seen in the patent to Lavon et al., U.S. Pat. No. 6,989,006 and the patent to Sherrod et al., U.S. Pat. No. 7,262,615. The Lavon et al. device teaches the complicated use of an openable pocket within a chassis, and a non-removable absorbable core component for placement of a removable core component thereon all within the chassis. Needless to say that the multiple absorbent members create the unsightly bulk heretofore identified. Similarly, the Sherrod et al. device incorporates absorbent inserts for use with an outer absorbent garment.

Still yet other prior art attempt to rectify the leakage problem as seen in the patent to Tears et al., U.S. Pat. No. 6,936,038, in which side walls form opposed channels bounding an absorbent core member. The channels are supposed to aid in the prevent of leakage, but the device with the channels results in unacceptable width making it uncomfortable to the wearer and unsightly.

SUMMARY OF THE INVENTION

In order to prevent leakage of bodily fluids during menstruation and the unsightly bulkiness of multiple absorbent components, the present invention discloses and teaches a disposable, substantially non-absorbent undergarment having a crotch region in combination with a sanitary napkin or panty liner member attached to the undergarment's crotch region. Upraised side ridges bounding the crotch region of the panty both eliminates leakage, without adding to bulk of the undergarment, and present a defined area where at least one panty liner unit of the panty liner member is attached. Preferably, the panty liner member will comprise up to three stacked, individual panty liners units each separated by a fluid impervious membrane adhered to the underside of each liner unit. The combination undergarment-panty liner is preferably manufactured as a one-piece article. However, alternatively, where the liner member and panty are separate pieces, the bottom most liner unit is fixed with a adhered disposable sheet. When the sheet is removed, an adhesive is exposed on the bottom most liner unit that permits attachment of the liner member to the crotch region of the panty so as to secure the liner member to the panty. In either case, when the upper most liner unit is soiled, it can be removed thereby exposing the next fresh liner unit. To the extent the panty gets soiled, it can be discarded as it is intended to be disposable.

It is thus an object of the present invention to provide a disposable panty undergarment that is substantially non-absorbent.

It is another object of the present invention to provide a disposable panty undergarment that is made of a thin disposable material such as cotton, paper, or polypropylene non-woven material.

It is still another object of the present invention to provide a disposable panty undergarment that has a crotch region that is bounded by upstanding ridges.

It is yet another object of the present device to provide a combination disposable panty undergarment having a crotch region with upstanding ridges with at least one absorbent panty liner unit or sanitary napkin member that is attached to the said crotch region.

BRIEF DESCRIPTION OF THE DRAWINGS

The above and other features and aspects of the present invention will become more apparent upon reading the following detailed description in conjunction with the accompanying drawings, in which.

DETAILED DESCRIPTION OF A PREFERRED EMBODIMENT

Figure 1:
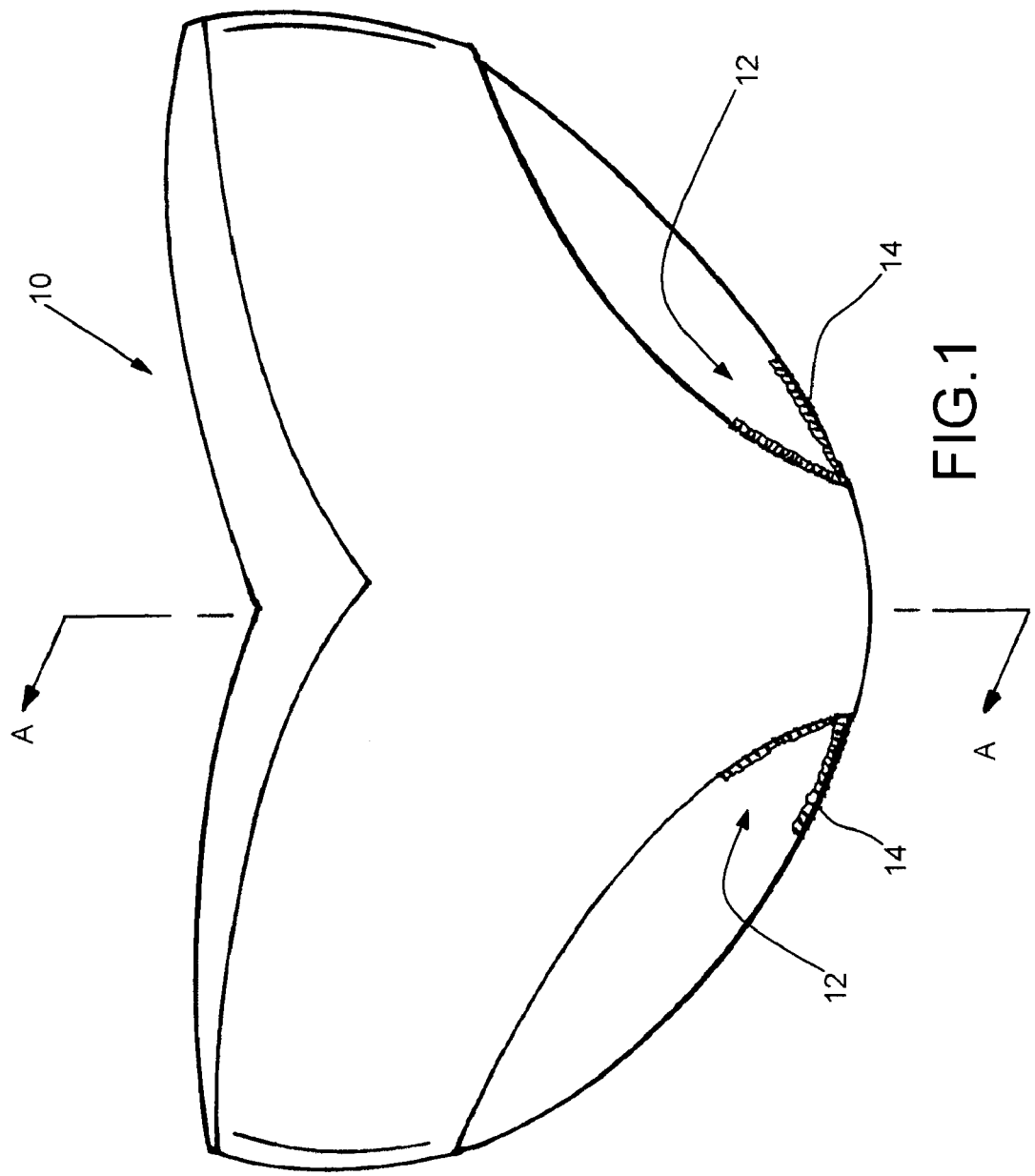
FIG. 1 is a front view of the present invention showing the disposable panty.

A disposable panty 10 of the present invention is shown and depicted in FIG. 1. The panty 10 may take the form of any style that customarily exists, such as the bikini style, the boy short style, or the thong style. The panty 10 in FIG. 1 is depicted in the bikini style.

The panty 10 is intended to be disposable, and therefore is constructed as conventionally known disposable undergarments. The panty 10 may be made of a solid material, such as cotton, paper, polypropylene, or biodegradable material, and may be made of a woven or non-woven material. The panty 10 may also come in a mesh (not shown) pattern. The panty therefore might be absorbent, or substantially non-absorbent. Accordingly, it is preferred for the panty 10 not to exceed 0.5 inches in thickness. To assist the panty 10 to conform to the shape of a user, elastic banding (not shown) may be incorporated into the waist and/or leg openings.

Figure 2:
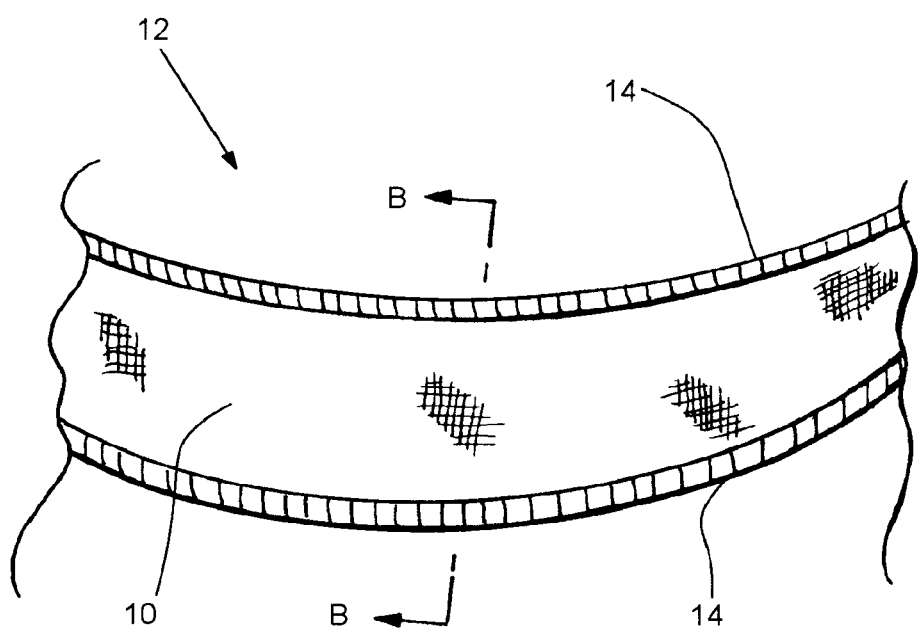
FIG. 2 is an exploded perspective view of the crotch region of the present invention taken along line A-A of FIG. 1.
Figure 3:
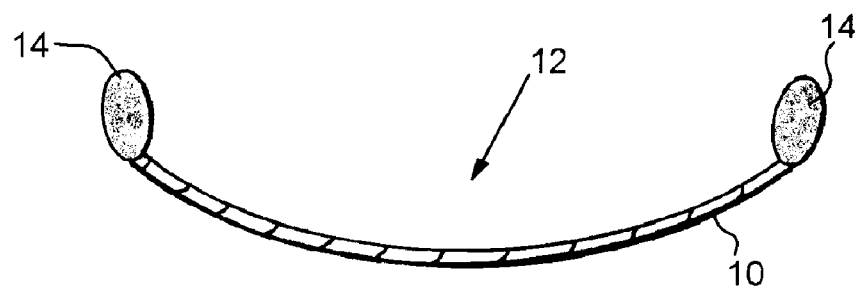
FIG. 3 is a cross section view of the present invention taken along line B-B of FIG. 2.

The panty 10 has a crotch region 12 that is formed on the interior of the panty 10. As more clearly shown in FIGS. 2 and 3, the crotch region 12 has lateral sides that terminate in upstanding ridges 14. The ridges 14 serve two purposes: to define a location to hold a panty line member, and to prevent leakage of bodily fluids during menstruation. The ridges 14 are constructed of a conventional elastic banding material; their dimensions approximate no greater than 1.0 inch in height, and no greater than 0.5 inches in width.

Figure 4:
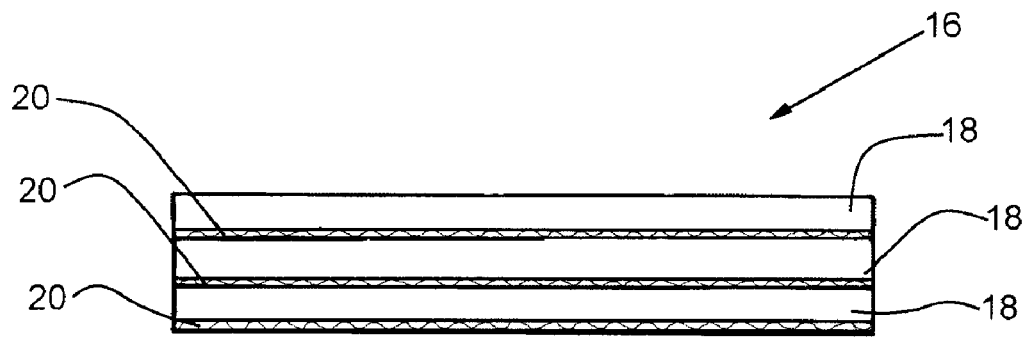
FIG. 4 is a side view of the panty liner member showing three panty liner units.
Figure 5:
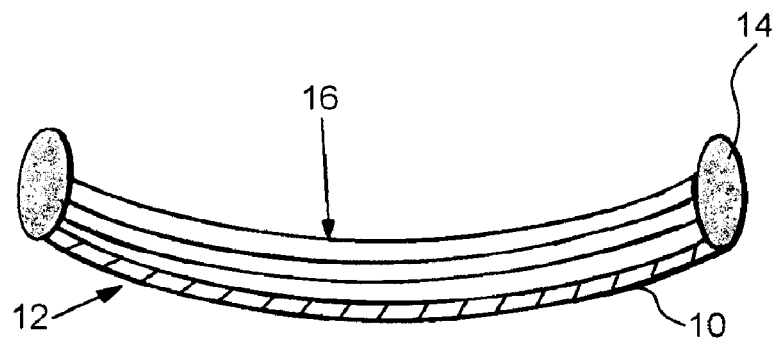
FIG. 5 is a cross section view of the crotch region of the present invention in combination with the panty liner member adhered thereto and showing three panty liner units.

FIG. 4 depicts the panty liner member 16 of the present invention 10. The panty liner member 16 comprises at least one panty liner unit 18. FIG. 4 shows three panty liner units 18. Each panty liner unit 18 is constructed of an absorbent material top layer for receiving, absorbing and containing bodily fluids during menstruation. Each panty liner unit 18 is sized to conform generally to the crotch region 12 of the panty 10. Each panty liner unit 18 has a bottom constructed of a fluid impervious layer 20. Each layer 20 is attached to the next lower unit 18 by an adhesive (not shown) such that when a soiled upper unit 18 is removed and discarded, the top of the next fresh unit 18 is exposed and ready to perform its receiving, absorbing and containing functions. FIG. 5 shows the panty liner member 16 affixed to the crotch region 12 of the panty 10 such that the ridges 14 act as a guide for placement of the liner member 16. In this regard, the panty 10 and panty liner member 16 may be constructed as a one-piece article. In the alternative, the panty liner member 16 and panty 10 may be constructed separately, where the bottommost panty unit 18 contains an adhesive (not shown) sufficient to allow the panty member 16 to be adhered to the panty 10 by the user.

In use, the user or wearer would put on the panty 10 with panty member 16 to collect and retain bodily fluids such as menses (though not intended for serious incontinence, the present invention could also collect a small amount of urine as the bodily fluid). Once the uppermost panty liner 18 was saturated with fluid, the wearer could remove that unit 18 thus exposing the next fresh unit. If however the collected fluid saturated the liner unit 18 to the point of soiling the panty 10, the panty 10 would be disposed of and a new one worn by the user.

In all cases it is understood that the above described embodiments are merely illustrative of the many possible specific embodiments which represent applications of the present invention. Numerous and varied other arrangements can be readily devised in accordance with the principles of the present invention without departing from the spirit and scope of the invention, as defined by the accompanying claims.

What is claimed is:

1. A disposable substantially non-absorbent, single layer panty having an inner and outer surface, and comprising a crotch region on top of said inner surface having lateral sides terminating in upstanding ridges, said panty being in combination with a substantially absorbent panty liner disposed therebetween the said sides and thereon said crotch region such that the said panty and liner comprise a one piece article.

2. The panty of claim 1, wherein said ridges are formed to a height of no greater than 1.0 inch in height and 0.5 inches in width.

3. The panty of claim 1, wherein the said panty is constructed of a thin or shear material such that the thickness of the panty is no greater than 0.5 inches in thickness.

4. A combination disposable single layer panty, and an attachable and removable panty liner member, wherein said panty comprises a crotch region having lateral sides terminating in upstanding ridges forming means for location and placement of said panty liner member thereon.

5. The combination disposable panty and panty liner member of claim 4, wherein the said panty liner member comprises at least one panty liner unit.

6. The combination disposable panty and panty liner member of claim 4, wherein the said panty liner member comprises no more than three panty liner units.

7. The combination disposable panty and panty liner member of claim 4, wherein the said panty liner member comprises a plurality of stacked panty liner units, each of said units comprising a absorbent top layer and a fluid impervious bottom layer.

8. The combination disposable panty and panty liner member of claim 7, wherein each said bottom layer is adhesively secured to the top of the next unexposed unit.

9. The combination disposable panty and panty liner member of claim 7, wherein the panty and panty liner member comprise a one-piece article.

10. The combination disposable panty and panty liner member of claim 7, wherein the panty and panty liner member comprise separate articles, such that the bottommost panty liner unit further comprises an adhesive for affixing said panty liner member to said panty.

* * * * *